United States Patent
Anderson et al.

(10) Patent No.: US 8,523,916 B2
(45) Date of Patent: Sep. 3, 2013

(54) METHODS AND DEVICES FOR SPINAL FIXATION ELEMENT PLACEMENT

(75) Inventors: David Greg Anderson, Moorestown, NJ (US); George Joseph Ross, Rehoboth, MA (US)

(73) Assignee: DePuy Synthes Products, LLC, Raynham, MA (US)

(*) Notice: Subject to any disclaimer, the term of this patent is extended or adjusted under 35 U.S.C. 154(b) by 744 days.

(21) Appl. No.: 12/700,504

(22) Filed: Feb. 4, 2010

(65) Prior Publication Data

US 2010/0137915 A1  Jun. 3, 2010

Related U.S. Application Data

(62) Division of application No. 10/737,537, filed on Dec. 16, 2003, now Pat. No. 7,666,188.

(51) Int. Cl.
*A61B 17/88* (2006.01)
(52) U.S. Cl.
USPC .......................................................... 606/279
(58) Field of Classification Search
USPC ................. 606/246, 264–267, 270, 279, 301, 606/86 A, 99, 104; 623/17.11
See application file for complete search history.

(56) References Cited

U.S. PATENT DOCUMENTS

| | | |
|---|---|---|
| 2,320,709 A | 6/1943 | Arnesen |
| 2,548,729 A | 4/1951 | Kumpman |
| 3,246,646 A | 4/1966 | Murphy |
| 3,552,799 A | 1/1971 | Koranda |
| 4,263,899 A | 4/1981 | Burgin |
| 4,461,281 A | 7/1984 | Carson |
| 4,537,448 A | 8/1985 | Ketterer |
| 4,545,374 A | 10/1985 | Jacobson |
| 4,573,448 A | 3/1986 | Kambin |

(Continued)

FOREIGN PATENT DOCUMENTS

| | | |
|---|---|---|
| DE | 3434807 | 12/1985 |
| DE | 10027988 A1 | 1/2002 |

(Continued)

OTHER PUBLICATIONS

Jampel, Robert and Charles Bloomgarden. "Individual extraocular muscle function from faradic stimulation of the oculomotor and trochlear nerves of the macaque," Investigative Opthamology, Jun. 1963, 265-266.

(Continued)

*Primary Examiner* — Eduardo C Robert
*Assistant Examiner* — David Comstock
(74) *Attorney, Agent, or Firm* — Nutter McClennen & Fish LLP

(57) ABSTRACT

Minimally invasive methods and devices are provided for positioning a spinal fixation element in relation to adjacent spinal anchors. In an exemplary embodiment, the device is a percutaneous access device that can be coupled to a spinal anchor, and the method includes the step of positioning a spinal fixation element through at least one sidewall opening of at least two percutaneous access devices such that the spinal fixation element extends in a lengthwise orientation that is substantially transverse to the longitudinal axis of each percutaneous access device. The spinal fixation element can then be advanced in the lengthwise orientation to seat the spinal fixation element in or adjacent to the receiver heads of at least two adjacent spinal anchors. A fastening element or other closure mechanism can then be applied to each spinal anchor to engage the spinal fixation element within the receiver heads of the adjacent anchors.

20 Claims, 14 Drawing Sheets

(56) References Cited

U.S. PATENT DOCUMENTS

| | | |
|---|---|---|
| 4,686,966 A | 8/1987 | Tsai |
| 4,765,311 A | 8/1988 | Kulik et al. |
| 4,872,451 A | 10/1989 | Moore et al. |
| 4,887,020 A | 12/1989 | Graham |
| 4,913,134 A | 4/1990 | Luque |
| 4,961,740 A | 10/1990 | Ray et al. |
| 5,015,255 A | 5/1991 | Kuslich |
| 5,024,659 A | 6/1991 | Sjostrom |
| 5,052,372 A | 10/1991 | Shapiro |
| 5,084,053 A | 1/1992 | Ender |
| 5,171,279 A | 12/1992 | Mathews |
| 5,231,973 A | 8/1993 | Dickie |
| 5,242,443 A | 9/1993 | Kambin |
| 5,242,446 A | 9/1993 | Steffee et al. |
| 5,324,290 A | 6/1994 | Zdeblick et al. |
| 5,357,983 A | 10/1994 | Mathews |
| 5,367,983 A | 11/1994 | Pound et al. |
| 5,395,317 A | 3/1995 | Kambin |
| 5,439,464 A | 8/1995 | Shapiro |
| 5,484,440 A | 1/1996 | Allard |
| 5,520,610 A | 5/1996 | Giglio et al. |
| 5,569,248 A | 10/1996 | Mathews |
| 5,647,873 A | 7/1997 | Errico et al. |
| 5,728,097 A | 3/1998 | Mathews |
| 5,741,261 A | 4/1998 | Moskovitz et al. |
| 5,749,884 A | 5/1998 | Benderev et al. |
| 5,762,629 A | 6/1998 | Kambin |
| 5,766,221 A | 6/1998 | Benderev et al. |
| 5,817,094 A | 10/1998 | Errico et al. |
| 5,891,147 A | 4/1999 | Moskovitz et al. |
| 5,897,590 A | 4/1999 | Donovan |
| 5,910,141 A | 6/1999 | Morrison et al. |
| 5,928,139 A | 7/1999 | Koros et al. |
| 5,931,777 A | 8/1999 | Sava |
| 5,954,635 A | 9/1999 | Foley et al. |
| 5,984,923 A | 11/1999 | Breard |
| 6,033,406 A | 3/2000 | Mathews |
| 6,139,493 A | 10/2000 | Koros et al. |
| 6,159,179 A | 12/2000 | Simonson |
| 6,183,472 B1 | 2/2001 | Lutz |
| 6,200,322 B1 | 3/2001 | Branch et al. |
| 6,224,545 B1 | 5/2001 | Cocchia et al. |
| 6,226,548 B1 | 5/2001 | Foley et al. |
| 6,235,028 B1 | 5/2001 | Brumfield et al. |
| 6,299,616 B1 | 10/2001 | Beger |
| 6,331,179 B1 | 12/2001 | Freid et al. |
| 6,371,968 B1 | 4/2002 | Kogasaka et al. |
| 6,440,133 B1 | 8/2002 | Beale et al. |
| 6,485,491 B1 | 11/2002 | Farris et al. |
| 6,520,907 B1 | 2/2003 | Foley et al. |
| 6,530,926 B1 | 3/2003 | Davison |
| 6,530,929 B1 | 3/2003 | Justis et al. |
| 6,540,749 B2 | 4/2003 | Schafer et al. |
| 6,554,831 B1 | 4/2003 | Rivard et al. |
| 6,607,530 B1 | 8/2003 | Carl et al. |
| 6,648,888 B1 | 11/2003 | Shluzas |
| 6,652,527 B2 | 11/2003 | Zucherman et al. |
| 6,660,006 B2 | 12/2003 | Markworth et al. |
| 6,666,891 B2 | 12/2003 | Boehm, Jr. et al. |
| 6,740,086 B2 | 5/2004 | Richelsoph |
| 6,740,089 B2 | 5/2004 | Haider |
| 6,743,231 B1 | 6/2004 | Gray et al. |
| 6,793,656 B1 | 9/2004 | Mathews |
| 6,821,277 B2 | 11/2004 | Teitelbaum |
| 6,849,064 B2 | 2/2005 | Hamada |
| 6,929,647 B2 | 8/2005 | Cohen |
| 7,083,261 B2 | 8/2006 | Silverbrook et al. |
| 7,083,621 B2 | 8/2006 | Shaolian et al. |
| 7,179,225 B2 | 2/2007 | Shluzas et al. |
| 7,179,261 B2 | 2/2007 | Sicvol et al. |
| 7,250,052 B2 | 7/2007 | Landry et al. |
| 7,306,603 B2 | 12/2007 | Boehm, Jr. et al. |
| 7,527,638 B2 | 5/2009 | Anderson et al. |
| 7,666,188 B2 | 2/2010 | Anderson et al. |
| 2001/0001119 A1 | 5/2001 | Lombardo |
| 2002/0011600 A1 | 1/2002 | Kurahashi et al. |
| 2002/0049368 A1 | 4/2002 | Ritland |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0116000 A1 | 8/2002 | Zucherman et al. |
| 2002/0116006 A1 | 8/2002 | Cohen |
| 2002/0123668 A1 | 9/2002 | Ritland |
| 2002/0138077 A1 | 9/2002 | Ferree |
| 2002/0161368 A1 | 10/2002 | Foley et al. |
| 2002/0169448 A1 | 11/2002 | Vanacker |
| 2002/0198526 A1 | 12/2002 | Shaolian et al. |
| 2003/0060826 A1 | 3/2003 | Foley et al. |
| 2003/0083657 A1 | 5/2003 | Drewry et al. |
| 2003/0083688 A1 | 5/2003 | Simonson |
| 2003/0083689 A1 | 5/2003 | Simonson |
| 2003/0130659 A1 | 7/2003 | Haider |
| 2003/0191371 A1 | 10/2003 | Smith et al. |
| 2003/0195549 A1 | 10/2003 | Davison et al. |
| 2003/0195550 A1 | 10/2003 | Davison et al. |
| 2003/0195551 A1 | 10/2003 | Davison et al. |
| 2003/0199885 A1 | 10/2003 | Davison et al. |
| 2003/0208203 A1 | 11/2003 | Lim et al. |
| 2003/0216768 A1 | 11/2003 | Gitis et al. |
| 2003/0229347 A1 | 12/2003 | Sherman et al. |
| 2004/0006301 A1 | 1/2004 | Sell et al. |
| 2004/0039384 A1 | 2/2004 | Boehm et al. |
| 2004/0082961 A1 | 4/2004 | Teitelbaum |
| 2004/0138662 A1 | 7/2004 | Landry et al. |
| 2004/0143265 A1 | 7/2004 | Landry et al. |
| 2004/0162560 A1 | 8/2004 | Raynor et al. |
| 2004/0172022 A1 | 9/2004 | Landry et al. |
| 2004/0260284 A1 | 12/2004 | Parker |
| 2004/0267277 A1 | 12/2004 | Zannis et al. |
| 2005/0038432 A1 | 2/2005 | Shaolian et al. |
| 2005/0038434 A1 | 2/2005 | Mathews |
| 2005/0065517 A1 | 3/2005 | Chin |
| 2005/0080418 A1 | 4/2005 | Simonson et al. |
| 2005/0085813 A1 | 4/2005 | Spitler et al. |
| 2005/0096748 A1 | 5/2005 | Yoon |
| 2005/0154389 A1 | 7/2005 | Selover et al. |
| 2005/0171540 A1 | 8/2005 | Lim et al. |
| 2005/0182410 A1 | 8/2005 | Jackson |
| 2005/0192570 A1 | 9/2005 | Jackson |
| 2005/0192579 A1 | 9/2005 | Jackson |
| 2007/0233097 A1 | 10/2007 | Anderson et al. |

FOREIGN PATENT DOCUMENTS

| | | |
|---|---|---|
| DE | 29810798 | 5/2004 |
| EP | 0528562 | 2/1993 |
| EP | 1190678 | 3/2002 |
| FR | 2729291 | 7/1996 |
| FR | 2796545 | 1/2001 |
| WO | 92/05742 A1 | 4/1992 |
| WO | 93/08745 A1 | 5/1993 |
| WO | 2004/004100 | 1/2004 |
| WO | 2004004100 A1 | 1/2004 |
| WO | 2004017847 A2 | 3/2004 |
| WO | 2005041799 A1 | 5/2005 |

OTHER PUBLICATIONS

Search Report from EP 04 81 2446 dated Dec. 2, 2008.

Wiltse LL and Spencer, CW, "New Uses and Refinements of the Paraspinal Approach," Jun. 6, 1988, Lippincott Williams and Wilkins, SPINE Jun. 1988;13(6):696-706.

Stephen L. Ritland, M.D., Surgical Technique: Micro-TLIF "A Mini-Open and Intermuscular Transforaminal Lumber Interbody Fusion," Aperture Spinal Access System, pp. 1-20, DePuy AcroMed, Inc., Raynham, MA (Oct. 2002).

"The Dilation Retractor System" product literature (4 pages) Bright Medical Instruments.

DePuy AcroMed Product Brochure "'micro'TLIF, A Mini-Open and Intermuscular Transforaminal Lumbar Interbody Fusion" Aperture Spinal System, (22 pages) Oct. 2002.

Foley, Kevin T., "CD Horizon SEXTANT Rod Insertion System Surgical Technique" Medtronic Sofamor Danek Product Brochure (32 pages) Jul. 2002.

Speer, et al., "An Arthroscopic Technique for Anterior Stabiliatin of the Shoulder with a Bioabsorbable Tack," J. Bone Joint Surg Am. 1996; 78:1801-7.

Muller, et al., "A Keyhole Approach for Endoscopically Assisted Pedicle Screw Fixation in Lumbar Spine Instability," Neurosurgery, vol. 47, No. 1, Jul. 2000.

METHODS AND DEVICES FOR SPINAL FIXATION ELEMENT PLACEMENT

CROSS REFERENCE TO RELATED APPLICATIONS

This application is a divisional of U.S. patent application Ser. No. 10/737,537, now U.S. Pat. No. 7,666,188, filed on Dec. 16, 2003 and entitled "Methods and Devices for Spinal Fixation Element Placement," which is hereby incorporated by reference in its entirety.

FIELD OF THE INVENTION

This application relates to tools for use in spinal surgery, and in particular to minimally invasive methods and devices for introducing a spinal fixation element to one or more spinal anchor sites within a patient's spine.

BACKGROUND OF THE INVENTION

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive devices and methods for implanting spinal fixation devices. One such method, for example, is disclosed in U.S. Pat. No. 6,530,929 of Justis et al. and it utilizes two percutaneous access devices for implanting an anchoring device, such as a spinal screw, into adjacent vertebrae. A spinal rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle. Moreover, the use of three separate access sites can undesirably lengthen the surgical procedure, and increase patient trauma and recovery time.

Accordingly, there remains a need for improved minimally invasive devices and methods for introducing a spinal fixation element into a patient's spine.

SUMMARY OF THE INVENTION

The present invention generally provides methods for introducing a spinal fixation element into a receiver head of adjacent spinal anchors. In one embodiment, the method utilizes at least two percutaneous access devices, each of which has a proximal end positioned outside a patient's body and a distal end coupled to a spinal anchor. The access device preferably includes at least one sidewall opening extending from the distal end through at least a portion of the percutaneous access device. In use, a spinal fixation element is positioned through the sidewall opening(s) in at least two adjacent percutaneous access devices such that the spinal fixation element extends in an orientation that is substantially transverse to a longitudinal axis of each percutaneous access device. The spinal fixation element is then advanced in the substantially transverse orientation to seat the spinal fixation element in or adjacent to the receiver head of at least two spinal anchors that are preferably implanted within adjacent vertebrae.

In an exemplary embodiment, each percutaneous access device includes first and second opposed sidewall openings, and at least one of the first and second sidewall openings extends from the distal end and terminates at a position distal to the proximal end. The percutaneous access devices can also optionally include a cannula, sleeve, or similar device disposed therearound that is effective to prevent removal of each percutaneous device from the spinal anchor coupled thereto. The sleeve preferably includes at least one sidewall opening formed therein that is adapted to align with the at least one sidewall opening in the percutaneous access device.

In another embodiment of the present invention, a percutaneous access system for introducing a spinal fixation element into a patient's body is provided. The system includes at least two spinal anchors that are adapted to be disposed in bone, at least one elongate, generally cylindrical hollow tube having at least one sidewall opening extending from the distal end thereof and terminating at a position distal to the proximal end, and a spinal fixation element. The system can also include at least one sleeve which is adapted to be slidably disposed around at least a portion of one of the hollow tubes. The sleeve(s) preferably includes at least one sidewall opening formed therein that is adapted to align with the sidewall opening(s) formed in the hollow tube. The system can also include a driver mechanism having a proximal handle portion, and a distal end that is adapted to couple to a spinal anchor such that rotation of the driver mechanism is effective to thread the spinal anchor into bone. The driver mechanism is preferably adapted to be disposed through the hollow tube(s).

DETAILED DESCRIPTION OF THE INVENTION

The present invention provides minimally invasive methods and devices for introducing a spinal fixation element into a surgical site in a patient's spinal column. In general, the method involves positioning a spinal fixation element through openings formed in at least two adjacent percutaneous access devices such that the spinal fixation element extends between the at least two adjacent percutaneous access devices in a lengthwise orientation. The spinal fixation element can then be advanced in a distal direction to seat the spinal fixation element in the receiver heads of the adjacent spinal anchors, or to otherwise position the spinal fixation element in relation to the adjacent spinal anchors. A fastening element or other closure mechanism can optionally be applied to each spinal anchor to engage the spinal fixation element within the receiver heads of the adjacent anchors, or to otherwise directly or indirectly connect the spinal fixation element to the anchors.

Figure 1:
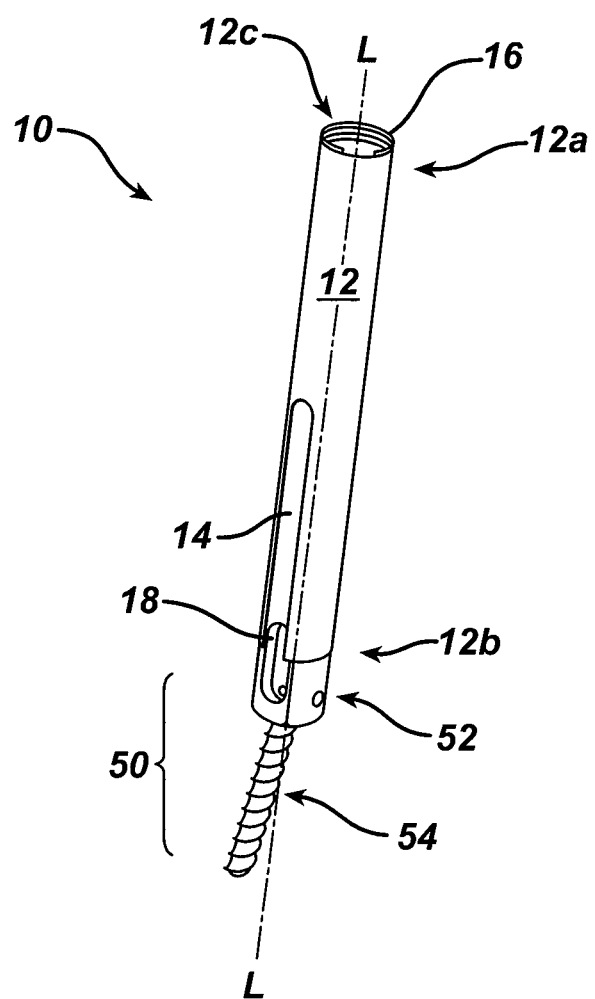
FIG. 1 is a perspective view of a percutaneous access device coupled to a spinal anchor according to one embodiment of the present invention.
Figure 2:
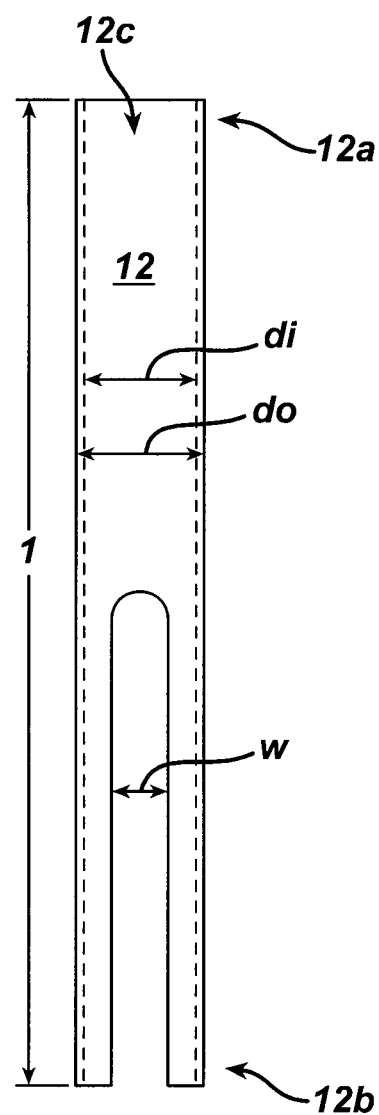
FIG. 2 is a cross-sectional view taken along the longitudinal axis L of the percutaneous access device shown in FIG. 1.

While a variety of devices can be used to perform the methods of the present invention, FIGS. 1 and 2 illustrate an exemplary embodiment of a percutaneous access device 12 that is mated to a spinal anchor 50 to form a spinal implant assembly 10. The device 12 is in the form of a generally elongate, cylindrical tube having an inner lumen 12c formed therein and defining a longitudinal axis L that extends between proximal and distal ends 12a, 12b. The size of the access device 12 can vary depending on the intended use, but it should have a length l that allows the proximal end 12a of the access device 12 to be positioned outside the patient's body, while the distal end 12b of the access device 12 is coupled to, or positioned adjacent to, a spinal anchor, e.g., anchor 50, that is disposed in a vertebra in a patient's spine. The inner diameter $d_i$ of the access device 12 can also vary depending on the intended use, but the inner diameter $d_i$ is preferably sufficient to accommodate a diameter or width of a spinal fixation element to be introduced therethrough.

The percutaneous access device 12 also preferably includes at least one sidewall opening or slot 14, and more preferably two opposed sidewall openings (only one opening 14 is shown), formed therein and extending proximally from the distal end 12b thereof. The openings 14 allow a spinal fixation element to be positioned lengthwise between two adjacent devices 12 such that the spinal fixation element extends in an orientation that is substantially transverse to the longitudinal axis L of the access devices 12, i.e., that crosses the longitudinal axis L of the access devices 12. The exact position of the spinal fixation element with respect to the longitudinal axis L will of course vary depending on the configuration of the spinal fixation element. The shape and size of the openings 14 can also vary depending on the configuration of the spinal fixation element, but the openings 14 preferably have a generally elongate shape with a width w that is sufficient to accommodate the diameter of the spinal fixation element. The openings 14 preferably extend over about half of the length, or more than half of the length, of the percutaneous access device 12. This allows a proximal portion of each opening 14 to be positioned outside a patient's body while the device 12 is in use, thus allowing a spinal fixation element to be externally positioned through the openings 14 and then moved distally to be implanted. A person skilled in the art will appreciate that the percutaneous access device 12 can include any number of sidewall openings having any shape that is sufficient to allow a spinal fixation element to be positioned therethrough.

Continuing to refer to FIG. 1, in use, the percutaneous access device 12 is preferably adapted to attach to a spinal anchor 50, and more preferably to the receiver head 52 of a spinal anchor 50. Accordingly, the distal end 12c of the percutaneous access device 12 can include one or more mating elements 18 formed thereon or therein for engaging the spinal anchor 50. Suitable mating elements include, for example, threads, a twist-lock engagement, a snap-on engagement, or any other technique known in the art, and in an exemplary embodiment the mating elements are formed on opposed inner surfaces of the distal end 12b of the access device 12. A sleeve (not shown) or other device, preferably having sidewall openings that correspond with the sidewall openings 14 formed in the percutaneous access device 12, can also be placed over the percutaneous access device 12, and optionally over the anchor 50 as well, to prevent disengagement of the access device 12 from the anchor 50 during use. Exemplary techniques for mating the percutaneous access device 12 to a spinal anchor are disclosed in U.S. Pat. No. 7,179,261, entitled "Percutaneous Access Devices and Bone Anchor Assemblies," filed on Dec. 16, 2003. A person skilled in the art will appreciate that a variety of other techniques can beused to removably mate the percutaneous access device to a spinal anchor.

Still referring to FIG. 1, an exemplary spinal anchor for use with the methods and devices of the present invention is shown. A person skilled in the art will appreciate that a variety of implants can be used with the devices and methods of the present invention, including, for example, spinal screws, hooks, bolts, and wires. By way of non-limiting example, FIG. 1 illustrates a spinal screw 50 that includes a distal, bone-engaging portion, e.g., a threaded shank 54, and a proximal, U-shaped, receiver head 52 that is adapted to seat a spinal fixation element, such as a spinal rod (not shown). The threaded shank 54 can be fixedly attached to the receiver head 52 to form a monoaxial screw, or alternatively the shank 54 can be configured as a polyaxial screw, as shown, that is rotatably disposed through an opening formed in the distal end of the receiver head 52 to allow rotation of the shank 54 with respect to the receiver head 52. A variety of techniques can be used to allow rotation of the head 52 with respect to the shank 54.

FIGS. 3A-13 show a minimally invasive method of implanting a spinal fixation element into the receiver heads of adjacent spinal anchors. While the method is shown and described in connection with the percutaneous access device 12 and spinal screw 50 disclosed herein, a person skilled in the art will appreciate that the method is not limited to use with such devices, and that a variety of other devices known in the art can be used. Moreover, while only two access devices 12, 12' and two implants 50, 50' are shown in FIGS. 8-13, the method of the present invention can be performed using any number of access devices and spinal anchors. The method can also be performed using only some of the method steps disclosed herein, and/or using other methods known in the art.

Figure 3A:
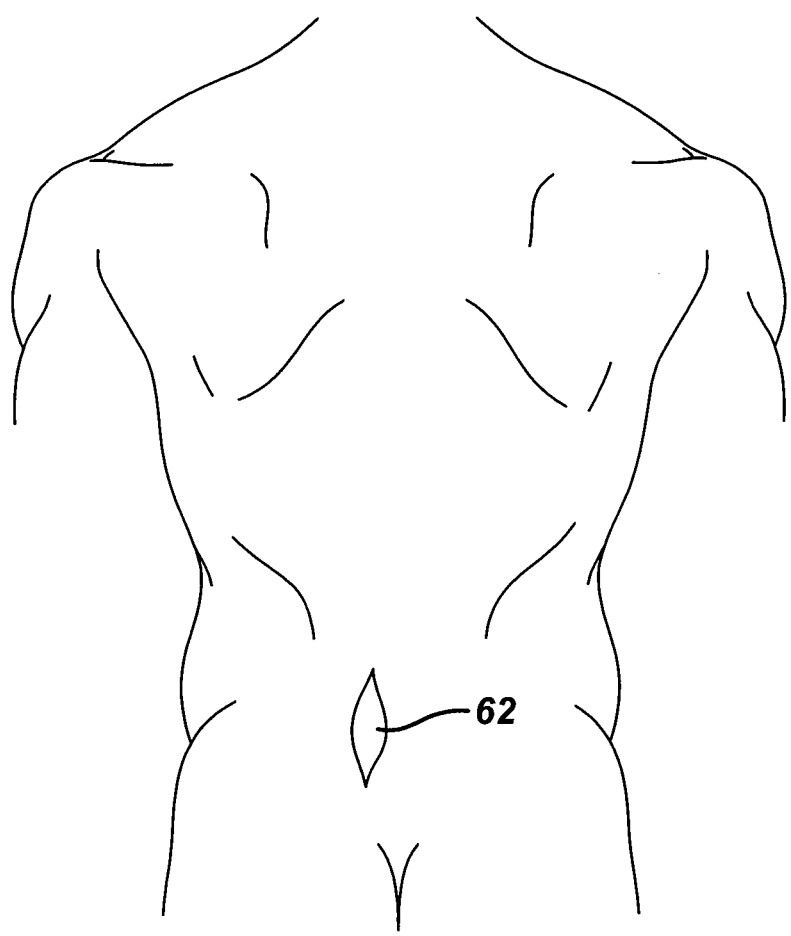
FIG. 3A is a posterior view of a midline incision formed in the thoracolumbar fascia of a patient's back.
Figure 3B:
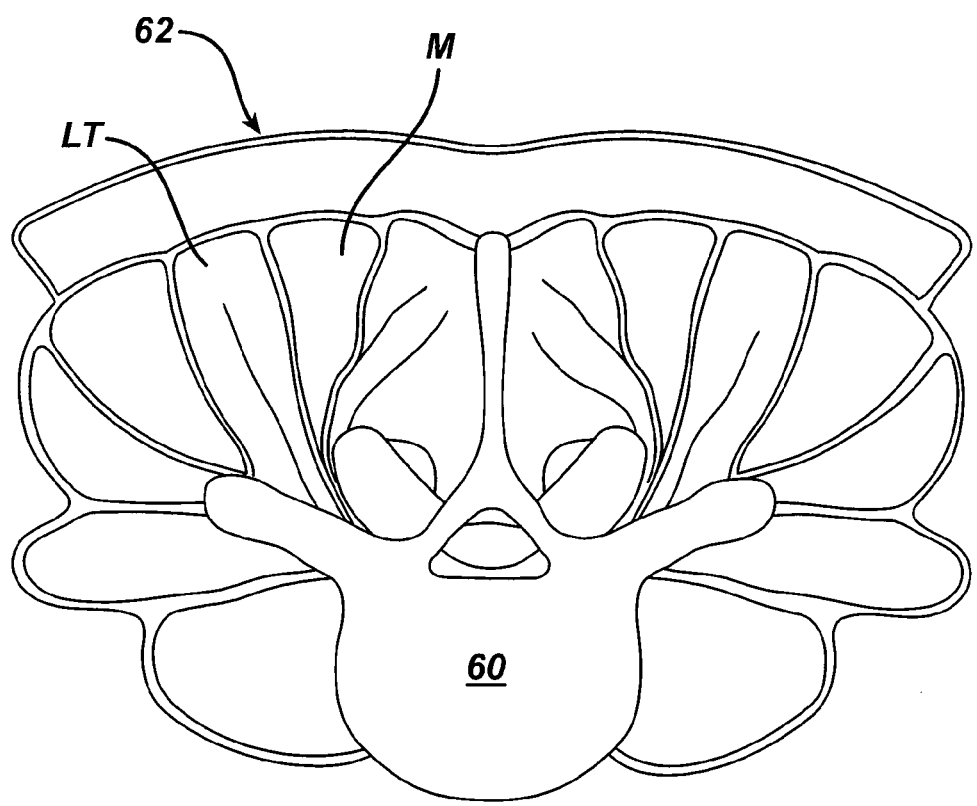
FIG. 3B is an end view showing a blunt dissection of the muscles surrounding a patient's vertebra.
Figure 4:
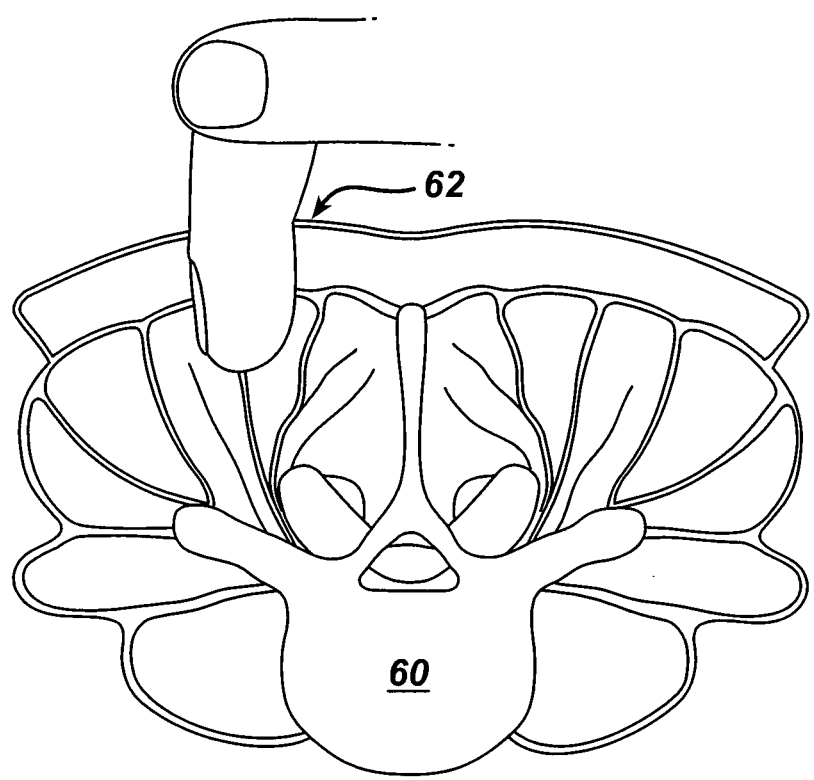
FIG. 4 is an end view of the vertebra shown in FIG. 3B showing a technique for separating the muscles along the muscle plane to gain access to the vertebra.

The procedure preferably begins by forming an incision through the tissue located adjacent to the desired implant site. While the location, shape, and size of the incision will depend on the type and quantity of spinal anchors being implanted, FIG. 3A illustrates a midline, blunt dissection incision 62 formed in the thoracolumbar fascia in the patient's back along the muscle plane. The length of the incision 62 is about 4-5 cm, however this can vary depending on the procedure. Once the midline incision 62 is formed, blunt finger dissection can be used, as shown in FIG. 4, to separate the longissimus thoracis and multifidus muscles, thereby exposing the facet and the junction of the transverse process and superior articular process.

Figure 5:
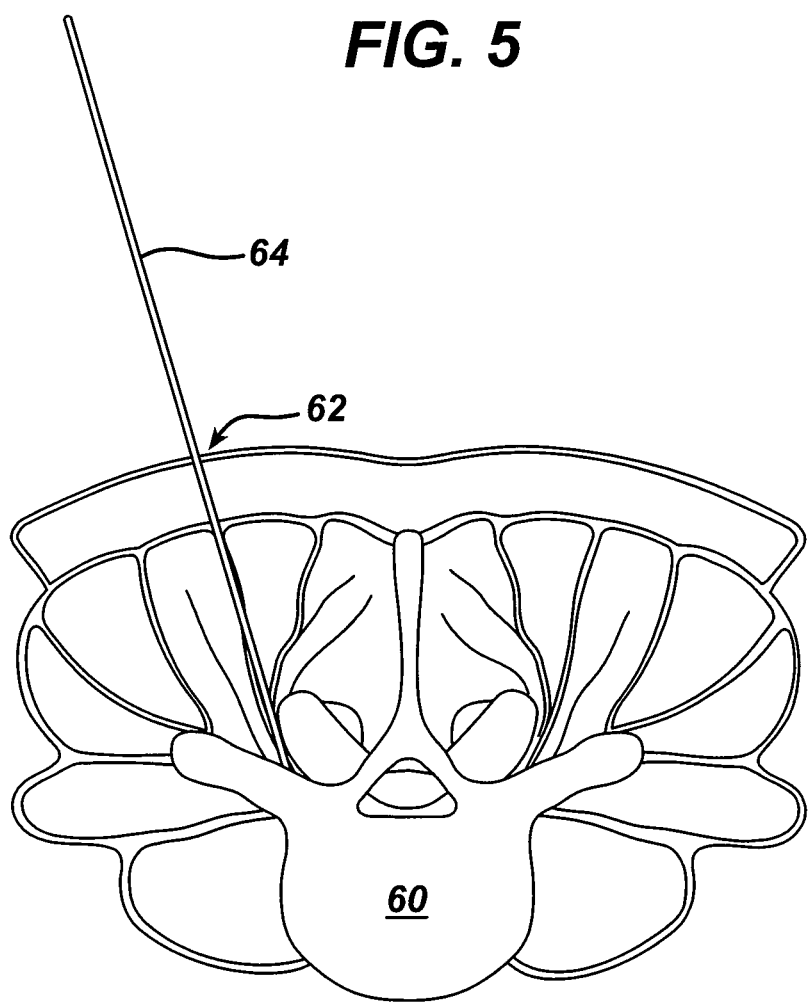
FIG. 5 is an end view of the vertebra shown in FIG. 4 showing placement of a k-wire through the incision and into the patient's vertebra.

As shown in FIG. 5, a guide wire, e.g., a k-wire 64, can be implanted, either prior to or after formation of the incision, at each spinal anchor implant site. The k-wire 64 preferably extends between the muscles and into the vertebra at the desired entry point of the spinal anchor. Fluoroscopy is typically used to facilitate proper placement of the k-wire 64.

Figure 6:
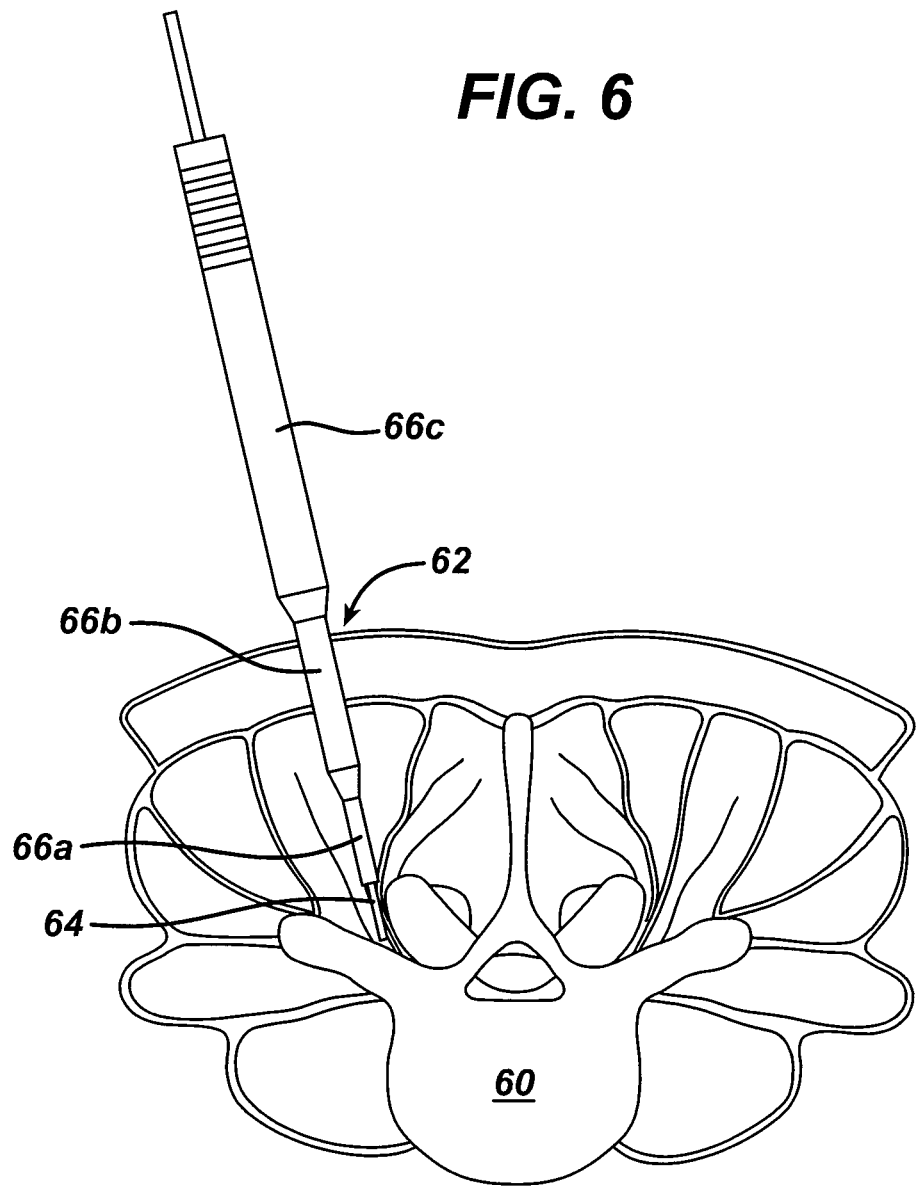
FIG. 6 is an end view of the vertebra shown in FIG. 5 having an obturator and several dilators disposed over the k-wire to dilate the tissue and muscles.

The opposed ends of the incision can then be dilated to provide a pathway for delivery of a spinal anchor to each implant site. FIG. 6 illustrates dilation at one end of the incision 62 using an obturator 66a having several dilators 66b, 66c of increasing size placed there over. The dilators 66b, 66c are delivered over the obturator 66a and k-wire 64 to essentially stretch the skin around the incision 62 and to expand the pathway to the anchor site. While not illustrated, a person skilled in the art will appreciate that the incision 62 can optionally be held opening using a refractor or an expandable cannula.

Figure 7:
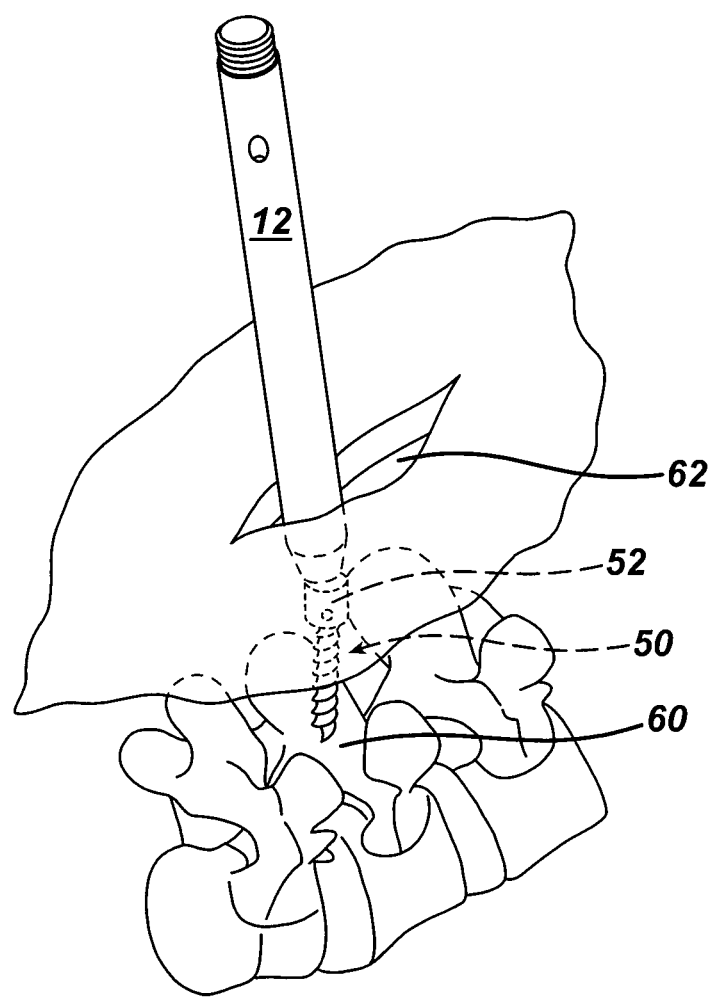
FIG. 7 is perspective view of a spinal anchor having a percutaneous access device coupled thereto and extending through an incision formed in the patient's tissue surface to implant the spinal anchor in a vertebra.

Once the incision 62 is dilated to the proper size, an anchor can be delivered to each anchor site, as shown in FIG. 7. This procedure typically involves preparation of the vertebra 60 using one or more bone preparation instruments, such as drills, taps, awls, burrs, probes, etc. While not always necessary, one or more cannulae can be used to provide a pathway from the incision 62 to the anchor site for insertion of the bone preparation instruments and/or the anchor. In an exemplary embodiment, a relatively small cannula is used to introduce bone preparation instruments into the surgical site. The incision 62 can then be further dilated, and the small cannula can be replaced with a larger cannula that is adapted to receive or mate to the anchor.

Once the vertebra 60 is prepared, a spinal anchor can be implanted at each implant site. An access device 12, 12' can be mated to each anchor 50, 50' after insertion of the anchor 50, 50' into bone 60, 60', but more preferably each percutaneous access device 12, 12' is attached to the anchor 50, 50' prior to insertion of the anchor 50, 50' into bone 60, 60' to provide a passageway for a driver tool for driving the anchor 50 into bone 60, 60'. FIG. 7 illustrates anchor 50 implanted in a first vertebra 60 and having access device 12 attached thereto. While not shown, the anchor 50 is preferably cannulated to allow the k-wire 64 to extend through the anchor 50 and the access device 12 to guide the devices 50, 12 toward the implant site. FIG. 7 further illustrates a second anchor 50' having an access device 12' mated thereto. As shown, the screw 50' is about to be implanted in a second vertebra 60' that is adjacent to the first vertebra 60. Once the screw 50' is positioned adjacent to the vertebra 60', a driver tool 200 can be positioned through the access device 12' and coupled to the receiver head 52' of the screw 50' to drive the screw 50' into the vertebra 60'.

In another embodiment, a sleeve can be placed over each access device 12, 12', either prior to or after the devices 12, 12', 50, 50' are implanted, to prevent the devices 12, 12' from becoming disengaged from the anchors 50, 50' to which they are attached. The sleeve (not shown) is preferably in the form of a cannula that has substantially the same configuration as each access device 12, 12'. The use of a sleeve is particularly desirable where the access devices 12, 12' utilize pin members that engage corresponding detents formed on an outer surface of each screw head 52, 52', as the sleeve will prevent the pin members from becoming disengaged from the detents. The sleeve can also optionally serve as an access device, allowing access devices 12, 12' to be detached and removed from the anchors 50, 50'.

Figure 8:
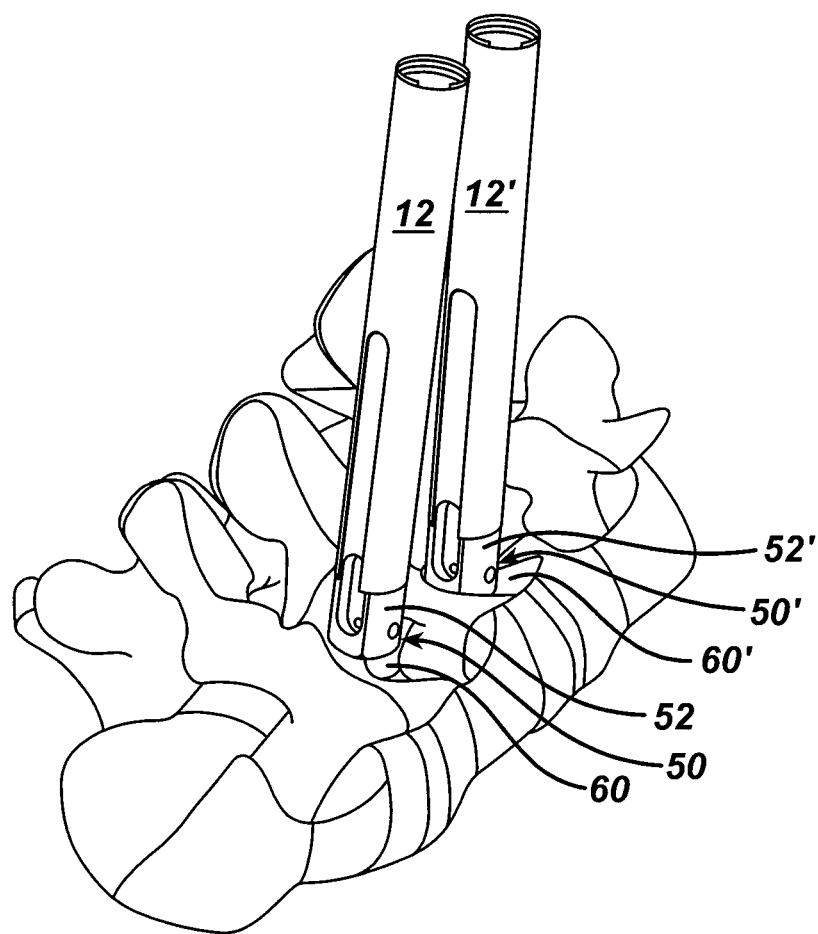
FIG. 8 is a perspective view of two percutaneous access devices attached to spinal anchors that are disposed within adjacent vertebrae in a patient's spinal column.
Figure 9:
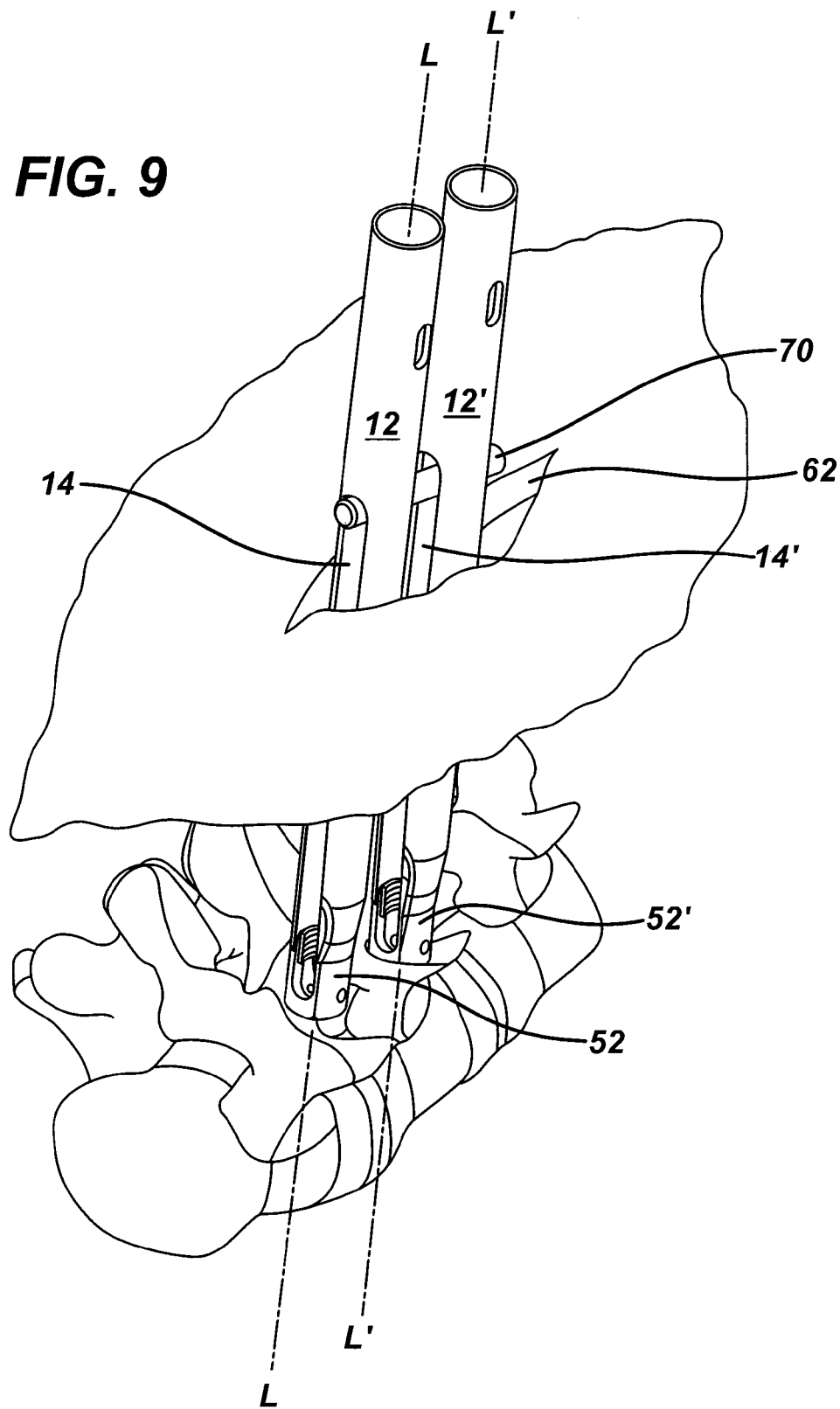
FIG. 9 illustrates a method for introducing a spinal fixation element through the percutaneous access devices shown in FIG. 8.

After the anchors are implanted, as shown in FIG. 8, a spinal fixation element is delivered to the anchor sites. As shown in FIG. 9, the spinal fixation element 70 is positioned through the openings 14, 14' in the adjacent devices 12, 12' such that the spinal fixation element 70 extends in a lengthwise orientation which is substantially transverse to the longitudinal axis L of the access devices 12, 12'. The exact angle of the fixation element 70 with respect to the percutaneous access devices 12, 12' will vary depending on the orientation of the access device 12, 12' with respect to the patient's spinal column, and it is understood that the orientation can vary during use since the percutaneous access devices 12, 12' can be oriented at various angles throughout the surgical procedure.

The spinal fixation element 70 is then moved distally toward the distal end 12b, 12b' of the percutaneous access devices 12, 12'. As the spinal fixation element 70 moves distally, it will advantageously pass between the muscles, thus eliminating the need to cut or tear tissue. The method is also particularly advantageous in that the percutaneous access devices 12, 12' direct the spinal fixation element 70 into the receiver heads 52, 52' of the adjacent spinal anchors 50, 50', thus allowing the spinal fixation element to be properly positioned without the necessity for direct visual access to the surgical site.

Figure 10:
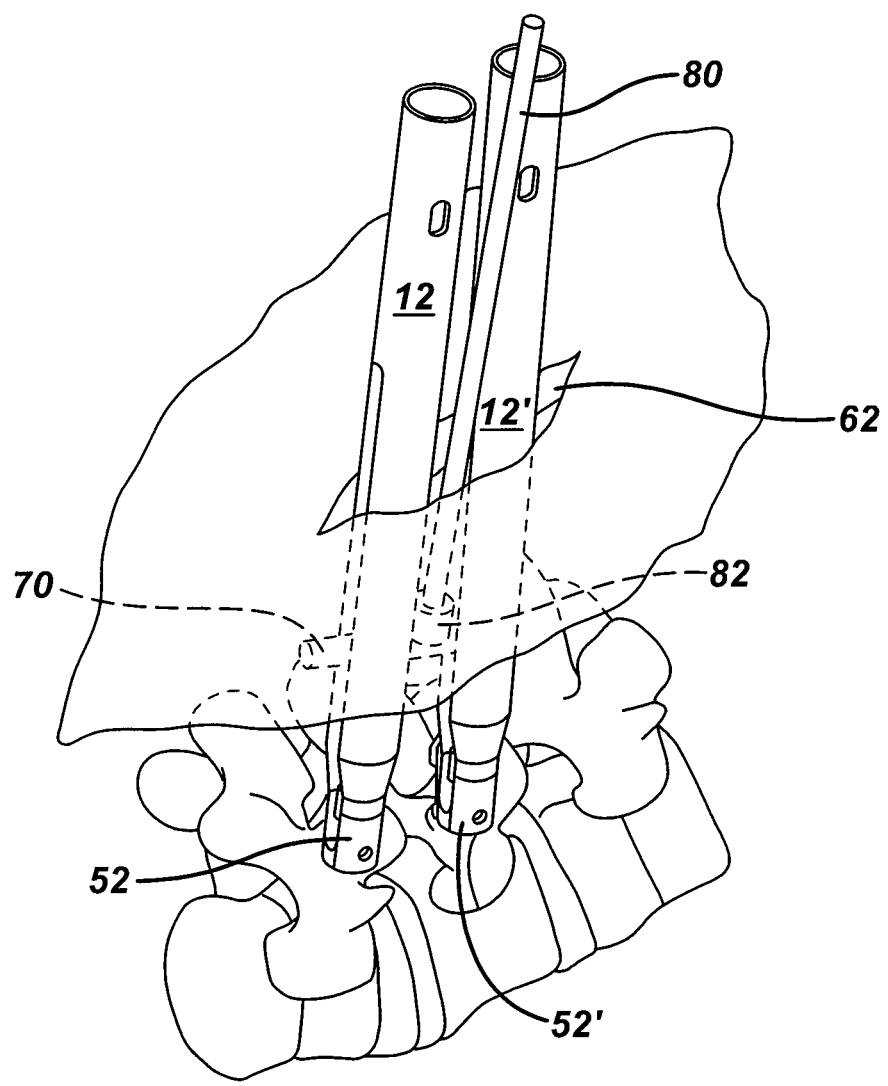
FIG. 10 is a perspective view of the spinal fixation element shown in FIG. 9 being advanced toward the spinal anchors using a pusher device.
Figure 11:
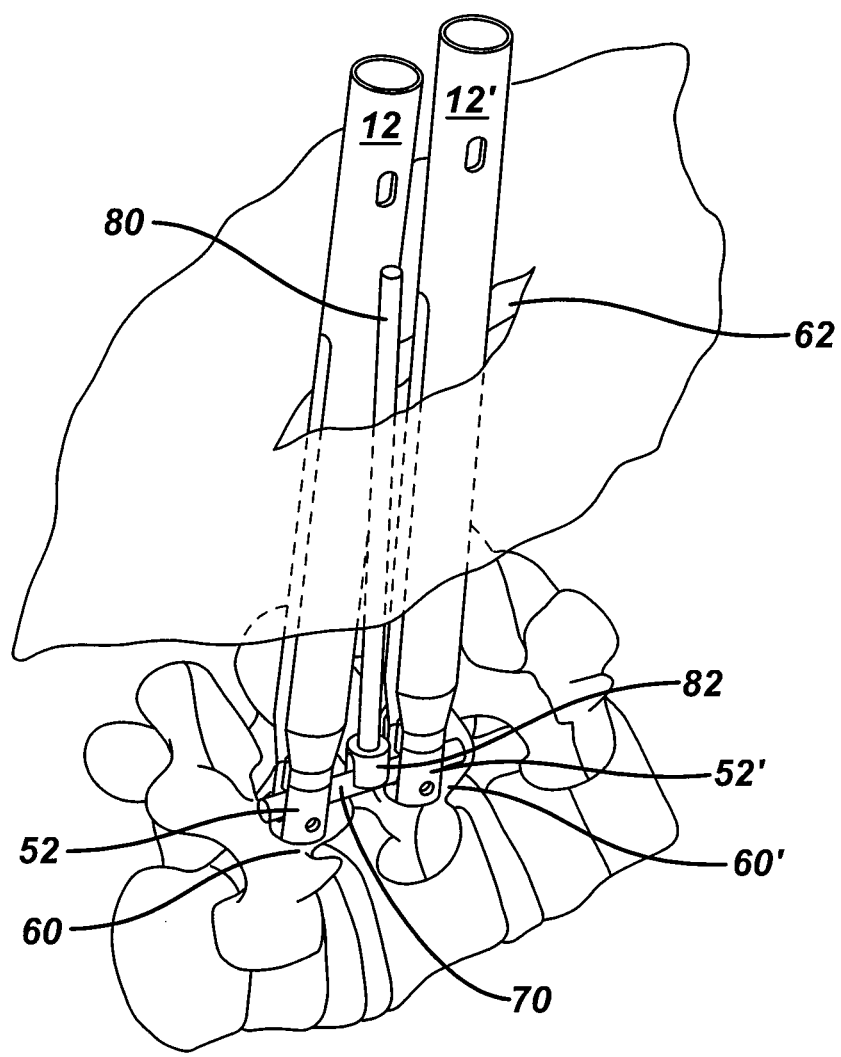
FIG. 11 is a perspective view of the spinal fixation element shown in FIG. 10 after it is fully positioned within receiver heads of the adjacent spinal anchors.

Movement of the spinal fixation element 70 in the distal direction can be achieved using pusher shaft 80, as shown in FIGS. 10 and 11. The pusher shaft 80 can have a variety of configurations, but it should be effective to allow controlled movement of the spinal fixation element 70. A person skilled in the art will appreciate that a variety of other techniques can be used to advance the spinal fixation element 70 distally between the percutaneous access devices 12, 12' to seat the spinal fixation element 70 into the receiver heads 52, 52' of adjacent spinal anchors 50, 50'. In the illustrated embodiment, the pusher shaft 80 includes a seating member 82 formed on a distal end thereof that is adapted to seat the spinal fixation element 70. The seating member 82, which is similar to a receiver head of a spinal anchor, is generally cylindrical and includes an open distal end with opposed U-shaped cut-out portions formed therein for receiving the spinal fixation element 70. In use, the seating member 82 is positioned around the spinal fixation element 70 and a force is applied to the pusher shaft 80 to move the spinal fixation element 70 distally.

Once the spinal fixation element 70 is fully seated in the receiver heads 52, 52' of the adjacent spinal anchors 50, 50', as shown in FIG. 11, the pusher shaft 80, if used, can then be removed or detached from the spinal fixation element 70, and a closure mechanism can be applied to one or both receiver heads 52, 52' to retain the spinal fixation element 70 therein. In an exemplary embodiment, however, a compression tool 100 is used to compress the access devices 12, 12' toward one another prior to applying a closure mechanism to each anchor 50, 50'. The closure mechanism(s) can, however, be partially applied before compression.

Figure 12:
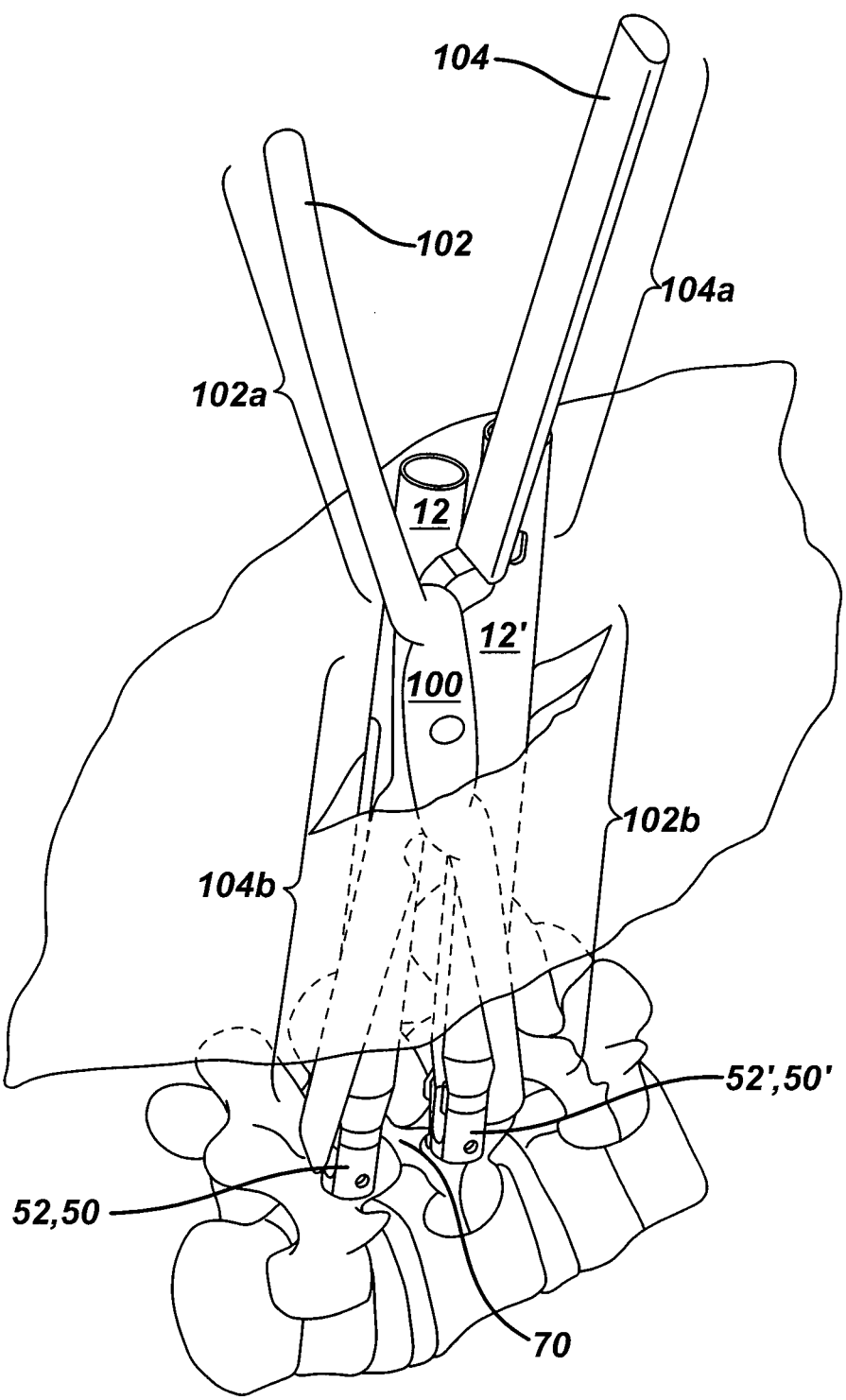
FIG. 12 is a perspective view of a compression tool positioned around the percutaneous access devices shown in FIG. 11 and compressing the devices toward one another.

An exemplary compression tool 100 is shown in FIG. 12, and in general it includes opposed arms 102, 104 that are pivotally coupled to one another at a substantial mid-point thereof such that each arm 102, 104 includes a distal portion 102b, 104b that is adapted to be disposed around a percutaneous access device 12, 12', and a proximal, handle portion 102a, 104a. The device 100 can also include a fulcrum (not shown) that is disposed between the arms 102, 104 to facilitate controlled movement of the arms 102, 104 with respect to one another. In use, the distal portion 102b, 104b of each arm 102, 104 is placed around an access device 12, 12', preferably around the distal end 12b, 12b' of each device 12, 12' and/or around the head 52, 52' of each anchor 50, 50'. The proximal, handle portions 102a, 104a are then brought toward one another to move the access devices 12, 12' toward one another, preferably while maintaining relative spacing therebetween, as shown in FIG. 12.

Figure 13:
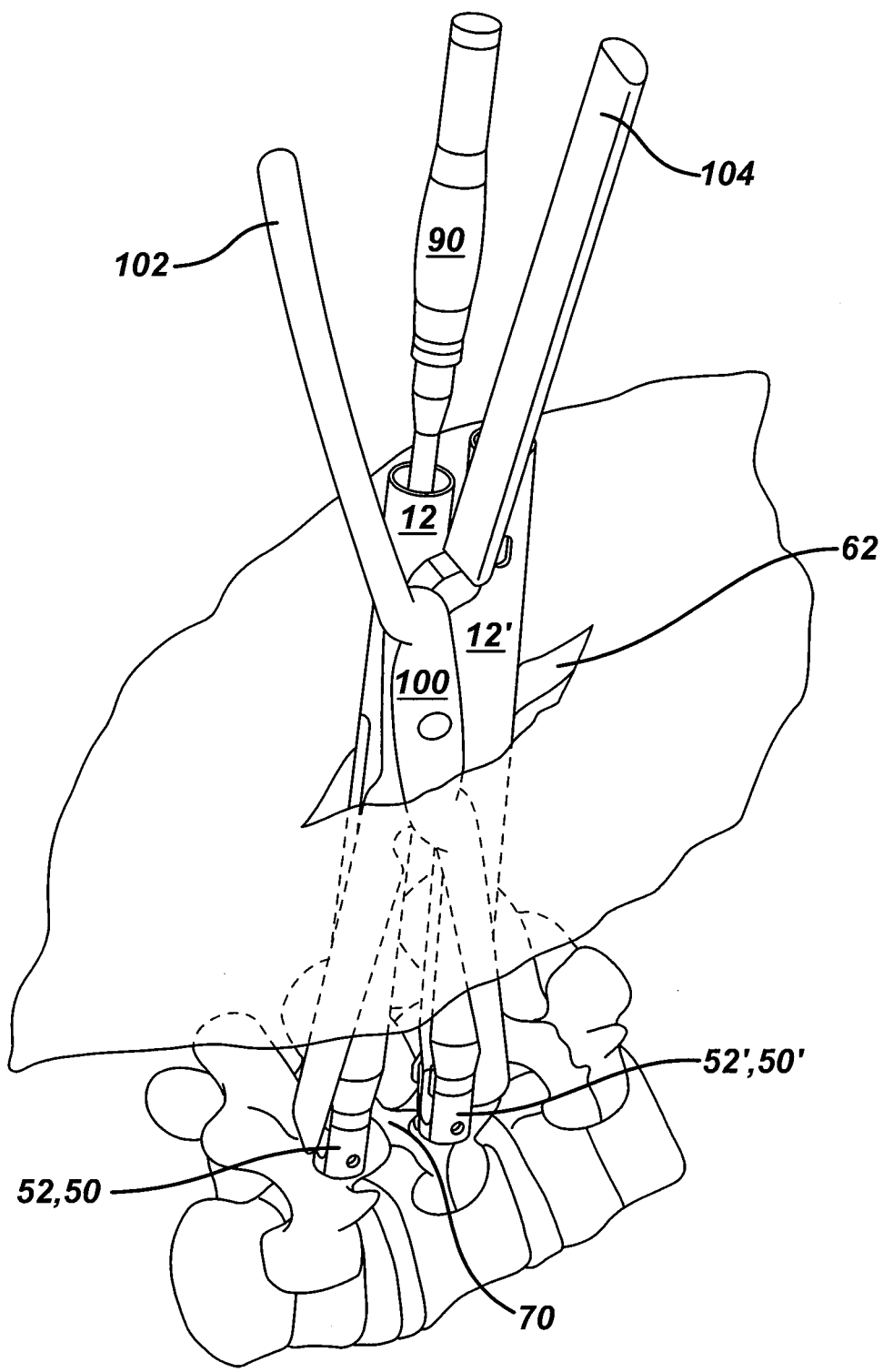
FIG. 13 is a perspective view of a closure mechanism being applied through one of the percutaneous access devices to lock the spinal fixation element in relation to the spinal anchor.

Once properly positioned, a closure mechanism can be applied, preferably via the access devices 12, 12', to each anchor head 50, 50' to retain the spinal fixation element 70 within the receiver heads 52, 52'. A variety of closure mechanisms and tools for delivering closure mechanisms are known in the art and they can be used with the present invention. By way of non-limiting example, FIG. 13 illustrates a driver tool 90 disposed through access device 12 for applying a closure mechanism, such as a set screw, to the receiver head 52 of the spinal anchor 50 to lock the spinal fixation element 70 with respect to the spinal anchor 50. This step can be repeated for the adjacent spinal anchor(s).

A person skilled in the art will appreciate that the spinal fixation element 70 does not need to be directly attached to each anchor 50, 50', and that it can be indirectly attached to the anchors 50, 50' using, for example, a band clamp, or slotted or offset connectors.

Once the fixation element 70 is secured in relation to the implants 50, 50', the access devices 12, 12' can be removed (if attached) from the implants 50, 50', leaving only a single, relatively small incision in the patient where each access device 12, 12' and the spinal fixation element 70 was introduced. This is particularly advantageous in that it reduces the amount of trauma caused to the patient, and it minimizes the damage to muscle surrounding the surgical site.

As previously stated, a person skilled in the art will appreciate that the method can be performed in any sequence using any of the steps. Moreover, the access devices of the present invention can be used to deliver multiple spinal fixation elements simultaneously or sequentially, and/or to perform a variety of other surgical procedures not illustrated or described herein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for introducing a spinal fixation element into a patient's spinal column, comprising:
   providing at least two percutaneous access devices, each device having
      a proximal end positioned outside a patient's body,
      a distal end coupled to a spinal anchor,
      a lumen extending between the proximal and distal ends of the percutaneous access device and defining a longitudinal axis, and
      at least one sidewall opening extending from the distal end through at least a portion of the percutaneous access device;
   positioning a spinal fixation element through the at least one sidewall opening and adjacent the proximal end of at least two percutaneous access devices such that the spinal fixation element extends in an orientation substantially transverse to the longitudinal axis of each percutaneous access device; and
   advancing the spinal fixation element in a distal direction along the longitudinal axis in the substantially transverse orientation to seat the spinal fixation element in a receiver head of at least two adjacent spinal anchors.

2. The method of claim 1, wherein each percutaneous access device includes first and second opposed sidewall openings.

3. The method of claim 1, wherein the at least one sidewall opening extends from the distal end and terminates at a position distal to the proximal end.

4. The method of claim 1, wherein each percutaneous access device includes a sleeve disposed therearound and effective to prevent removal of each percutaneous device from the spinal anchor coupled thereto, the sleeve including at least one sidewall opening formed therein that is adapted to align with the at least one sidewall opening in the percutaneous access device.

5. The method of claim 1, wherein each percutaneous access device is threadably coupled to the receiver head of each spinal anchor.

6. The method of claim 1, wherein each percutaneous access device and spinal anchor are mating together by a twist-lock closure mechanism.

7. The method of claim 1, wherein each percutaneous access device is coupled to the receiver head of a spinal anchor, and the at least one opening in the percutaneous access device is adapted to align with a seating portion formed in each receiver head.

8. The method of claim 1, further comprising providing a pusher mechanism adapted to advance the spinal fixation element into the receiver head of adjacent spinal anchors.

9. The method of claim 1, further comprising providing a compression tool, and engaging at least two adjacent percutaneous access devices to compress the devices toward one another while maintaining relative spacing therebetween.

10. The method of claim 9, wherein the compression tool comprises first and second opposed arms that are pivotally mated to one another.

11. The method of claim 1, further comprising delivering a closure mechanism through each percutaneous access device and applying the closure mechanism to each spinal anchor to lock the spinal fixation element in the receiver heads of the anchors.

12. A method for introducing a spinal fixation element into a receiver head of adjacent spinal anchors, comprising:

positioning a spinal fixation element through openings formed in at least two adjacent percutaneous access devices such that the spinal fixation element extends between the at least two adjacent percutaneous access devices in a lengthwise orientation adjacent a proximal portion of the at least two percutaneous access devices;

advancing the spinal fixation element in a distal direction to seat the spinal fixation element in the receiver heads of the adjacent spinal anchors.

13. The method of claim 12, wherein the spinal fixation element is advanced between muscles.

14. The method of claim 12, wherein the each spinal anchor is coupled to a percutaneous access device.

15. The method of claim 12, wherein each percutaneous access device includes opposed openings formed therethrough and extending along a length thereof.

16. The method of claim 15, wherein the openings comprise slots that extend from a distal end and terminate at a position distal to the proximal end of each percutaneous access device.

17. The method of claim 12, further comprising providing a pusher mechanism adapted to advance the spinal fixation element into the receiver head of adjacent spinal anchors.

18. The method of claim 12, further comprising providing a compression tool, and engaging at least two adjacent percutaneous access devices to compress the devices toward one another.

19. The method of claim 18, wherein the compression tool comprises first and second opposed arms that are pivotally mated to one another.

20. The method of claim 12, further comprising providing and applying a closure mechanism to each spinal anchor to lock the spinal fixation element in the receiver heads of the anchors.

\* \* \* \* \*